US00PP36889P2

(12) United States Plant Patent
Hansen

(10) Patent No.: US PP36,889 P2
(45) Date of Patent: Aug. 12, 2025

(54) ***YUCCA* PLANT NAMED 'Dragon Slayer'**

(50) Latin Name: ***Yucca pallida* x *filamentosa***
Varietal Denomination: Dragon Slayer

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,374

(22) Filed: Dec. 20, 2024

(51) Int. Cl.
*A01H 5/12* (2018.01)
*A01H 5/02* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12; A01H 5/02
See application file for complete search history.

*Primary Examiner* — Kent L Bell

(57) ABSTRACT

A new and unique *Yucca* plant named 'Dragon Slayer' is characterized by a rounded-mound of stiff, linear-lanceolate bluish-green leaves that are flat with concave apices and margins that produce few marginal filifers. The plant produces a loose colony that is winter hardy. The creamy-white flowers are produced on attractive, compact, heavily-branched, upright panicles in the summer. The new plant is suitable for the garden or as a potted plant in the garden or home.

2 Drawing Sheets

Botanical classification: *Yucca pallida* x *filamentosa.*
Variety denomination: 'Dragon Slayer'.

STATEMENT REGARDING PRIOR DISCLOSURES UNDER 37 CFR 1.77 (b) (6)

The first offer for *Yucca* 'Dragon Slayer' sales was by Walters Gardens, Inc. to Prides Corner Farms on Jan. 15, 2024. The new plant was subsequently on Dec. 1, 2024, offered on a website operated by Walters Gardens, Inc. Walters Gardens, Inc. obtained the new plant and all the information about the new plant from the inventor.

BACKGROUND OF THE INVENTION

The present invention relates to the new and distinct *Yucca* plant, *Yucca* 'Dragon Slayer', referred to herein by the cultivar name 'Dragon Slayer' and the new plant. 'Dragon Slayer' was hybridized by the inventor in the summer of 2017 at a wholesale perennial nursery in Zeeland, Michigan as a cross between the proprietary hybrid known only by the breeder code 14- 3-19 as the female or seed parent and a proprietary unnamed selection of *Yucca filamentosa* as the male or pollen parent.

The new plant has been successfully asexually propagated by division of the rhizomes since 2020 and by sterile shoot-tip tissue culture at the same wholesale perennial nursery. Both methods of asexual propagation have been found to produce stable and identical plants that maintain all the unique characteristics of the original plant in successive generations.

BRIEF SUMMARY OF THE INVENTION

'Dragon Slayer' differs from all other *Yucca* plants known to the Inventor. The nearest comparison plants are: 'Powder Blue' (not patented), 'Hairy' (not patented), and 'Silver Anniversary' U.S. Plant Pat. No. 31,437.

'Powder Blue' has a lighter blue foliage color. 'Hairy' has more marginal filaments, more intense bluish foliage, more leaves per stem and the leaves are narrower. 'Silver Anniversary' is a hybrid of *Yucca filamentosa* and *pallida* which has a taller habit with taller burgundy-colored scapes, and the foliage is narrower, more upright, and more numerous.

The female parent plant has a very narrow subtle chartreuse margin, the leaf center is bluish, with fewer leaves per stem, the leaves lack marginal filifers, thinner flower stems, and less flowers per stem. The male parent has more leaves per stem, the leaves are less bluish, with more filifers on the margin, and the flower stems are taller with more flowers.

'Dragon Slayer' is unique from all the above cultivars in possessing the following combined traits:

1. Numerous leaves are acaulescent, lanceolate, straight, flat with concave apex, bluish-green;
2. Habit is loose colony;
3. Creamy-white flowers are on heavily-branched, paniculate, upright, compact stalks;

BRIEF DESCRIPTION OF THE DRAWING

The drawings of *Yucca* 'Dragon Slayer' demonstrate the overall appearance of the new plant including the unique traits as two-year-old plants grown in a full-sun garden in Zeeland, Michigan. The colors are as accurate as reasonably possible with color reproductions. Ambient light spectrum, temperature, source, and direction may cause the appearance of minor variations in color.

DETAILED BOTANICAL DESCRIPTION

Figure 1:
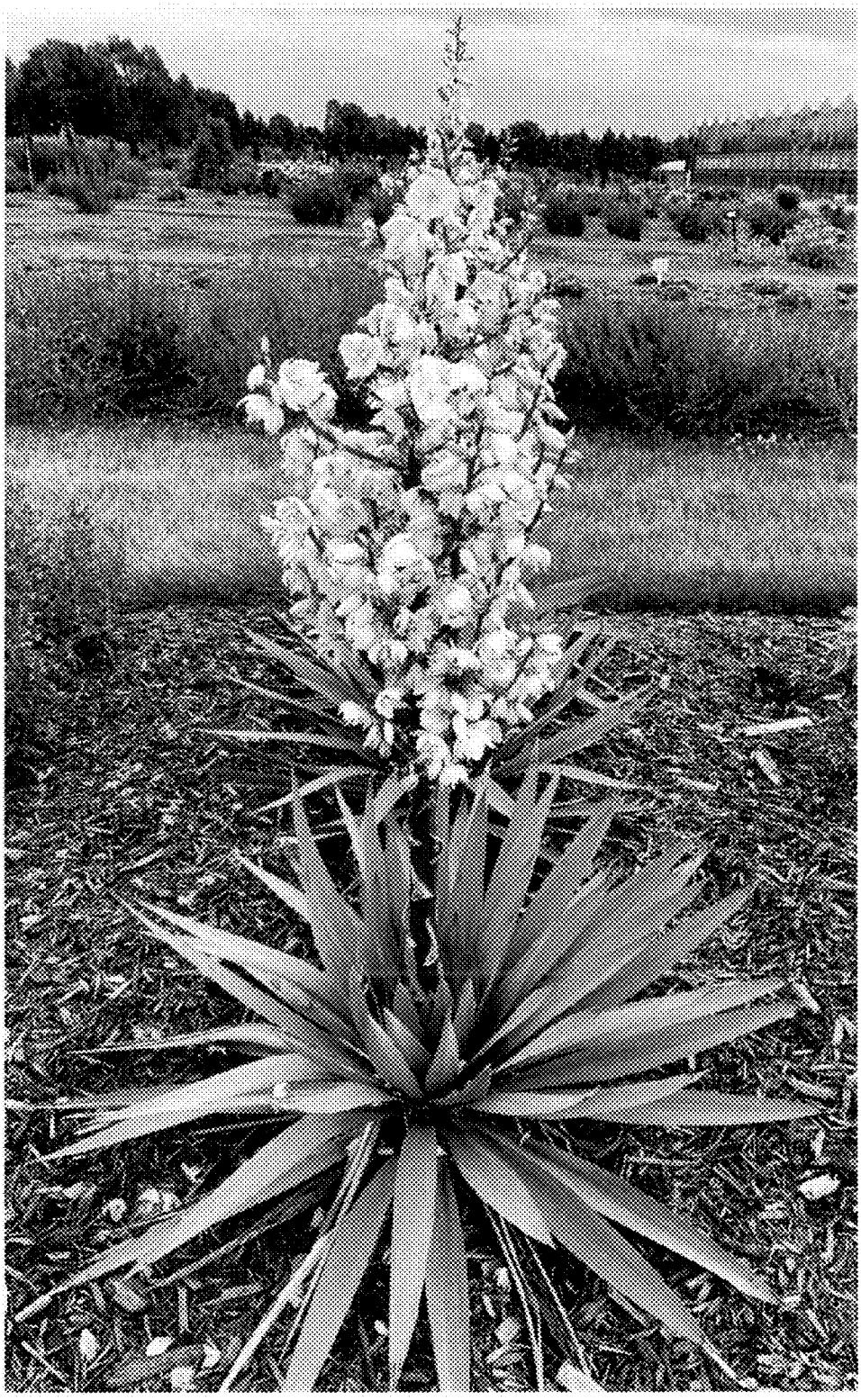
FIG. 1 shows the habit of the new plant in full flower from the side angle.
Figure 2:
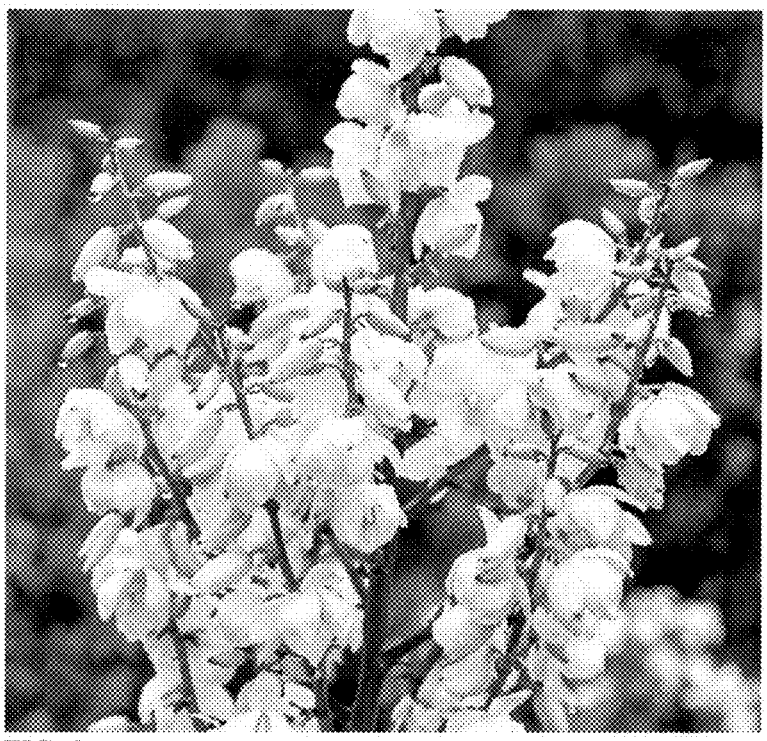
FIG. 2 shows a close-up of the flowers.
Figure 3:
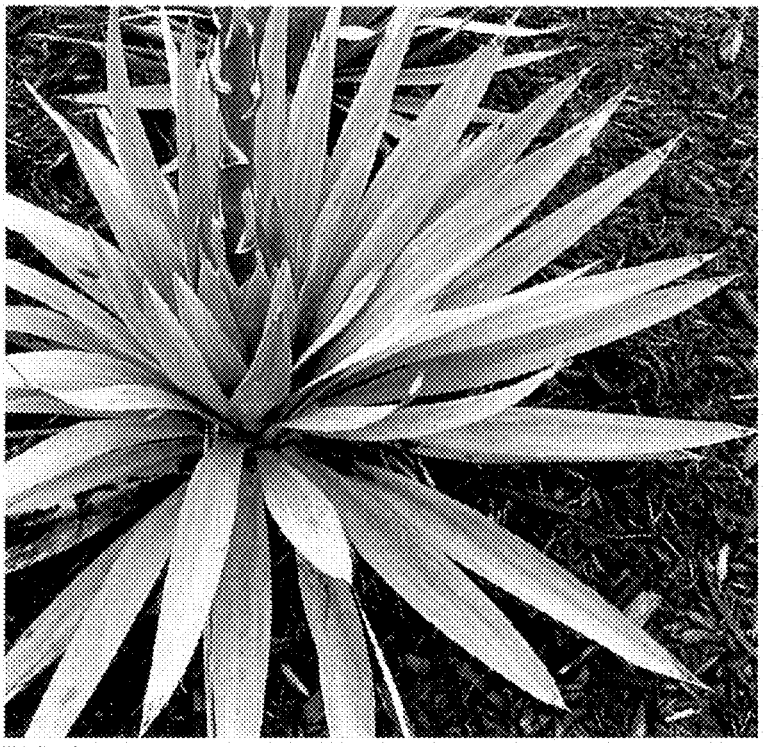
FIG. 3 shows a close-up of the foliage and scape base.

The following descriptions and color references are based on the 2015 edition of The Royal Horticultural Society Colour Chart except where common dictionary terms are used. The new plant, *Yucca* 'Dragon Slayer', has not been observed under all possible environments. The phenotype may vary slightly with different environmental conditions, such as temperature, light, fertility, moisture, and maturity levels, but without any change in the genotype. The following observations and size descriptions are of two-year-old plants in a full-sun garden in Zeeland, Michigan.

Parentage: The female or seed parent is the proprietary hybrid 14-3-19, the male parent is a proprietary unnamed selection of *Yucca filamentosa;*

Propagation: By shoot tip cuttings and sterile shoot-tip tissue culture;

Time to initiate roots from tissue culture: About 21 days;

Growth rate: Moderate;

Crop time: About 20 to 28 weeks to finish in a 3.8-liter container from a 35 mm tissue culture growing at about 21° C.;

Rooting habit: Fleshy, lightly branching, with roots up to 30 cm long;

Root color: Nearest RHS NN155B;

Plant shape and habit: Succulent herbaceous perennial with basal rosettes of leaves radially emerging from a central stem and arching distally, producing a radially-symmetrical rounded mound with about 5 stems per plant;

Plant size: Foliage height about 47 cm tall from the soil line to the top of the leaves and 130 cm. wide, scape height to about 178 cm tall;

Stem: To about 4 cm across; covered with foliage;

Foliage description: Linear to lanceolate; simple; sessile; bi-laterally symmetrical; coriaceous; apex concaved distally, narrowly acute with terminal mucro; base truncate; dentate; spirally arranged; adaxial and abaxial glabrous; abaxial slightly scaberulous; margin with random filifers slightly irregularly reflexed; to about 5 cm long from the margin and about 0.1 mm wide;

Mucro (apical spine): About 8 mm long and 1 mm wide at base; sharp; firm;

Foliage fragrance: None observed;

Leaf number: About 50 per mature division;

Leaf size: 48.5 cm long and 4.5 cm wide.

Leaf blade color:

*Adaxial*.—young between RHS 122C and RHS 188C, and mature between RHS N138B and RHS 191A with the apical margin nearest RHS 200A.

*Abaxial*.—Young between RHS 122C and RHS 188C, and mature between RHS N138B and RHS 191A with apical margin nearest RHS 200A.

*Filifers*.—Nearest RHS 161C.

*Mucro color*.—Young expanding nearest RHS 139A, mature between RHS 199B and RHS 199C.

Petiole: Leaves sessile;

Veins: Parallel; color not distinct abaxial or adaxial;

Inflorescence: Flowering portion to about 130 cm tall and about 85 cm across; with about 350 to 500 flowers per inflorescence;

Peduncle: Terete; glaucous; glabrous; stiff; strong; highly-branched; rigidly upright; about 178 cm long and 3 cm diameter below first flowers; with about 50 branches to about 19 cm long and about 8 mm diameter at base; branches outwardly at about a 60-degree to 45-degree angle above horizontal;

Peduncle color: Basal portion before flowering nearest a blend between RHS N77C and RHS 177B, basal portion during flowering nearest RHS 200B, distal portion and branches between RHS N199A and RHS NN137B;

Pedicel: Not present, flowers sessile;

Inflorescence bracts: About 9 below branches and subtending branches; below branches obtuse with broad, truncate, partially-clasping base, and acute apex, about 6 cm long, 2.5 cm across at base, 1 cm across in middle, and 1.5 cm across about 4 cm from base, decreasing in size distally; bracts at branches deltoid with truncate base and sharply acute apex, about 3 cm long and 2.2 cm wide at base; margins entire; simple; glabrous;

Bract color: Initially between RHS N77C and RHS 199A, drying before flower open to nearest RHS 199D;

Buds one day prior to opening: Oblong ellipsoidal; acute apex; truncate base; about 4 cm long and about 1.5 cm across at widest portion near middle;

Bud color: Nearest RHS NN155D with a light blush of nearest RHS 157C and a random presence of a light blush nearest RHS 64D;

Flower description: Perfect; incomplete; zygomorphic; about 3 cm long and opening to about 5.5 cm across; lasting about 3 to 4 days per flower; flowering period about three weeks in summer;

Flower fragrance: Not detected;

Tepals: Six in two imbricate sets; outer set oblong-lanceolate with acute apex; inner set obtuse with rounded apex; both sets with truncate base, margin entire, glaucous and glabrous abaxial and adaxial, and slightly concavo-convex; to about 3.3 cm long; outer set to about 2.2 cm wide; inner set to about 3 cm wide;

Tepal color: Adaxial nearest RHS NN155C with nearest RHS 157B concentrated toward base; abaxial nearest RHS NN155D with a light blush of nearest RHS 157C;

Androecium: Six;

*Filaments*.—Six; applanate; straight; about 5 mm long, 2 mm across; color nearest RHS 157A.

*Anther*.—Basifixed; longitudinal; oblong elliptical; about 14 mm long prior to dehiscing and about 4mm diameter; color nearest RHS 155A.

*Pollen*.—Not observed.

Gynoecium: Single; three-chambered; superior; to about 28 mm long;

*Style*.—Three; 12 mm long and 3 mm wide at base; color nearest RHS NN155B.

*Stigma*.—About 2 mm wide, 1 mm long; color nearest RHS NN155A.

*Ovary*.—Superior; about 12 mm long and 5 mm across at base; color between RHS 146D and RHS 145D.

Fruit and seed: Not yet observed;

Disease resistance and pest: *Yucca* 'Dragon Slayer' has not been observed to be resistant or susceptible to diseases and pests beyond that which is normal for other *Yucca*. The new plant is xeromorphic and survives well with minimal water once established. The new plant is winter hardy to USDA zone 5. Full extent of winter hardiness has not been tested.

It is claimed:

1. A new and distinct cultivar of ornamental *Yucca* plant named 'Dragon Slayer' as herein described and illustrated.

* * * * *